US008293493B2

(12) United States Patent
Coll et al.

(10) Patent No.: US 8,293,493 B2
(45) Date of Patent: Oct. 23, 2012

(54) THROMBIN GENERATION DETERMINATION METHOD

(75) Inventors: Enriqueta Coll, Orlando, FL (US); Ali Amirkosravi, Longwood, FL (US); John Francis, Longwood, FL (US)

(73) Assignee: Adventist Health System/Sunbelt, Inc., Orlando, FL (US)

( * ) Notice: Subject to any disclaimer, the term of this patent is extended or adjusted under 35 U.S.C. 154(b) by 362 days.

(21) Appl. No.: 12/694,318

(22) Filed: Jan. 27, 2010

(65) Prior Publication Data

US 2011/0183365 A1   Jul. 28, 2011

(51) Int. Cl.
*C12Q 1/56* (2006.01)
(52) U.S. Cl. .......................... 435/13; 436/69
(58) Field of Classification Search .................. 435/13; 436/69
See application file for complete search history.

(56) References Cited

U.S. PATENT DOCUMENTS

| 4,543,335 | A | * | 9/1985 | Sommer et al. ............ 436/69 |
| 5,192,689 | A | | 3/1993 | Hemker et al. |
| 6,936,430 | B1 | | 8/2005 | Krilis |
| 2009/0311730 | A1 | | 12/2009 | Hemker et al. |
| 2011/0045512 | A1 | * | 2/2011 | Hemker et al. ............ 435/13 |

FOREIGN PATENT DOCUMENTS

WO   2006/117246 A1   11/2006
WO   2008052795 A1   5/2008

OTHER PUBLICATIONS

Chandler W. et al. Optimization of Plasma Fluorogenic Thrombin Generation Assays. Coagulation and Transfusion Medicine, American J Clinical Pathology 132:169-179, 2009.*
Tapp H. et al. Calibrating Thrombin Generation in Different Samples: Less Effort with a Less Efficient Substrate. The Open Atherosclerosis & Thrombosis J vol. 2, 6-11, 2009.*
FLx800 Fluorescence Microplate Reader, Product Specification [online]. BIOTEK, 2009 [retrieved on Mar. 7, 2011]. Retrieved from the Internet <URL: http://replay.waybackmachine.org/20090225075943/http://www.biotek.com/products/microplate_detection/flx800_fluorescence_microplate_reader.html>.
Hemker, H.C., Wielders, S., Kessels, H. and Beguin, S.; Continuous Registration of Thrombin Generation in Plasma, Its Use for the Determination of the Thrombin Potential, Thrombosis and Haemostasis, 1993, pp. 617-624, vol. 70(4), F.K. Schattauer Verlagsgesellschaft mbH (Stuttgart).
Hemker, H. Coenraad and Beguin, Suzette; Thrombin Generation in Plasma: Its Assessment Via the Endogenous Thrombin Potential, Thrombosis and Haemostasis, 1995, pp. 134-138, vol. 74(1), F.K. Schattauer Verlagsgesellschaft mbH (Stuttgart).
Hemker, H . Coenraad, Giesen, Peter L.A., Ramjee, Manoj, Wagenvoord, Rob, and Benguin, Suzette; The Thrombogram: Monitoring Thrombin Generation in Platelet Rich Plasma, Thrombosis and Haemostasis, 2000, pp. 589-591, vol. 83, F.K. Schattauer Verlagsgesellschaft mbH (Stuttgart).
Ramjee, Manoj; The Use of Fluorogenic Substrates to Monitor Thrombin Generation for the Analysis of Plasma and Whole Blood Coagulation, Analytical Biochemistry, 2000, pp. 11-18, vol. 277, Academic Press.
Hemker, H.C., Giesen, P., Aldieri, R., Regnault, V., Desmed, E., Wagenvoord, R., Lecompte, T. and Beguin, S.; The Calibrated Automated Thrombogram (CAT): a universal routine test for hyper-and hypocoagulability, Pathophysiology of Haemostasis and Thrombosis, 2002, pp. 249-253, vol. 32, Karger.
Hemker, H. Coenraad, Giesen, Peter, Al Dieri, Raed, Regnault, Veronique, De Smedt, Eric, Wagenvoord, Rob, Lecompte, Thomas, and Beguin, Suzette; Calibrated Automated Thrombin Generation Measurement in Clotting Plasma, Pathophysiology of Haemostasis and Thrombosis, 2003, pp. 4-15, vol. 33, Karger.
Tappenden, Kerry A., Gallimore, Michael J., Evans, Gillian, Mackie, Ian J., and Jones, David W.; Thrombin Generation: A Comparison of Assays Using Platelet-Poor and -Rich Plasma and Whole Blood Samples from Healthy Controls and Patients with a History of Venous Thromboembolism, British Journal of Haematology, 2007, pp. 106-112, vol. 139, Blackwell Publishing Ltd.
Al Dieri, Raed and Hemker, Coen H.; Thrombin Generation in Whole Blood; Journal Compilation, correspondence, British Journal of Haematology, 2008, pp. 895-908, vol. 141, Blackwell Publishing Ltd.
Tappenden, K.A., Gallimore, M.J., Evans, G., Mackie, I.J., and Jones, D.W.; Thrombin Generation in Whole Blood—Response to Al Dieri & Hemker, Journal Compilation, correspondence, British Journal of Haematology, 2008.
Berntorp, Erik and Salvagno, Gian Luca, Standardization and Clinical Utility of Thrombin-Generation Assays, Seminars in Thrombosis and Hemostasis, 2008, pp. 670-682, vol. 34, No. 7.
Coll, E, Amirkhosravi, A., Francis, J.; Detection of Tissue Factor Activity in Whole Blood by a Fluorogenic Thrombin Generation Assay; International Society for Thrombosis and Hemostasis, Boston, Jul. 11-16, 2009; poster presentation.
Nijhuis S., Apitz-Castro R., Hemker C.H.; Thrombin Generation in a Thin Layer of Whole Blood, Journal of Thrombosis and Haemostasis, 2009, vol. 7, Supplement 2: Abstract PP-TH-155.

* cited by examiner

*Primary Examiner* — Ralph Gitomer
(74) *Attorney, Agent, or Firm* — GrayRobinson, P.A.; Carl M. Napolitano

(57) ABSTRACT

A method for measuring a generation of thrombin in a sample of whole blood as a function of time includes adding to a sample of whole blood a fluorogenic substrate and a thrombin activator to form an activated sample. A conversion product is permitted to form in the activated sample. Fluorescence is measured as a function of time from a fluorescent group that is released during the formation of the conversion product with the use of a fluorescence detector. The fluorescence detector operates in an extended range mode and has an increased sensitivity. Thrombin generation as a function of time can then be calculated from the measured fluorescence as a function of time.

11 Claims, 3 Drawing Sheets

THROMBIN GENERATION DETERMINATION METHOD

BACKGROUND OF THE INVENTION

1. Field of the Invention

The present invention relates to blood assays, and, more particularly, to methods for assaying thrombin generation, and, most particularly, to methods for assaying thrombin generation in a whole blood sample.

2. Description of Related Art

The coagulation of blood occurs through a complex series of reactions that function as a biological amplifier and culminate in the conversion of soluble circulating fibrinogen into a fibrin meshwork at the site of a vascular injury, providing stability to a hemostatic plug of platelets. In this system, relatively few initiating substances sequentially and proteolytically activate a cascade of circulating precursor proteins, the coagulation factor enzymes.

Among the reactions is the conversion of prothrombin to thrombin, which is the pivotal enzyme of the coagulation system. Thrombin is a serine protease that rapidly activates platelets and converts fibrinogen to insoluble fibrin. Thrombin also converts FXIII to FXIIIa, which chemically cross-links the fibrin clot.

Abnormalities in the coagulation cascade can have potentially fatal effects, leading to extremes of bleeding disorders and excessive clotting, thrombosis.

It is known to assess the coagulation system by activating the cascade and measuring the time it takes for the sample blood or plasma to clot. Although clotting times provide clinically useful information, they actually only represent the initial (<5%) thrombin generation. The majority of thrombin is formed after this initial period.

Attempts have been made to quantify the dynamics of thrombin formation. Hemker et al. have devised a commonly used technique ("Thrombin Generation in Plasma: Its Assessment via the Endogenous Thrombin Potential," *Thrombosis and Haemostasis* 74, 134-38, 1995; "Continuous Registration of Thrombin Generation in Plasma, Its Use for the Determination of the Thrombin Potential, *Thrombosis and Haemostasis* 70, 617-24, 1993; "The Thrombogram: Monitoring Thrombin Generation in Platelet Rich Plasma," *Thrombosis and Haemostasis* 83, 589-91, 2000; "Calibrated Automated Thrombin Generation Measurement in Clotting Plasma," *Pathophysiology Haemostasis and Thrombosis* 33, 4-15, 2003; the contents of all of which are incorporated hereinto by reference).

The techniques of Hemker et al. include the addition of a thrombin activator to a plasma sample together with a fluorogenic thrombin substrate. Thrombin formed during the clotting reaction consumes the substrate, producing a conversion product that is detected fluorometrically in real time. From these data can be calculated the endogenous thrombin potential (ETP), which indicates how much thrombin has been active and for how long. The data can also be used to calculate a lag time (the time to formation of thrombin), the maximal thrombin concentration reached, and the time to the peak thrombin formation.

What has not been successfully achieved, however, is the measurement of thrombin generation in whole blood, primarily owing to fluorescence signal quenching by red blood cells.

SUMMARY OF THE INVENTION

The present invention is directed to a method for measuring a generation of thrombin in a sample of whole blood as a function of time. The method comprises adding to a sample of whole blood a fluorogenic substrate and a thrombin activator to form an activated sample. A conversion product is permitted to form in the activated sample. Fluorescence is measured as a function of time from a fluorescent group that is released during the formation of the conversion product with the use of a fluorescence detector. The fluorescence detector operates in an extended range mode and has an increased sensitivity. Thrombin generation as a function of time can then be calculated from the measured fluorescence as a function of time.

Thrombin is the pivotal molecule in the coagulation process, and is generated through the cooperation of plasma proteins and blood cells. The importance of platelets in the coagulation process is also well established, as is that of white blood cells. While red blood cells are less active, in a small percentage of them, the outer membrane exhibits procoagulant ability.

It is therefore believed that it is preferable to use whole blood rather than plasma to evaluate the overall thrombin generation capacity of blood, with all the cellular and plasmatic components (i.e., platelets, monocytes, and coagulation and fibrinolytic plasma proteins) in their natural environment. The present invention allows the calculation of the time course of thrombin activity in whole blood as a complete entity under controlled conditions, providing a measure of the amount of active thrombin that is present in the blood during the clotting process. The present assay therefore provides a reliable measurement method for hemostasis and thrombosis studies.

A major problem associated with studying thrombin generation in whole blood has been the quenching of fluorescence by red blood cells. The present invention solves this problem by capturing the fluorescence signals that are stable and consistent, and follow typical performance characteristics of thrombin generation assays, allowing the calculation of all thrombin generation parameters.

The present method is also advantageous as it enables the measurement of thrombin generation in a whole blood sample that is minimally manipulated and diluted. Several samples can be assayed at the same time using 5 replicates and 2 calibrator wells. The type and amount of synthetic fluorogenic thrombin substrate added to the sample is substantially exactly the same as for the plasma samples (e.g., Z-Gly-Gly-Arg-AMC). No additional devices are needed beyond a fluorescent plate reader having a high sensitivity photomultiplier and the capacity to extend the reading range.

The present method can be used to evaluate hypo- and hyper-coagulable conditions. As thrombotic diseases, such as coronary infarction, stroke, pulmonary embolism, etc., are responsible for approximately one-half of death and disability in Western society, the present method can be useful for evaluating the pro-thrombotic capacity of a patient. The method can also therefore provide valuable research data in comparing coagulability data between patient groups, following treatment protocols and results, studying drug benefits in reducing thrombin generation of the blood, and developing improved assays and apparatus for coagulation measurement.

DETAILED DESCRIPTION OF THE PREFERRED EMBODIMENTS

Figure 1:
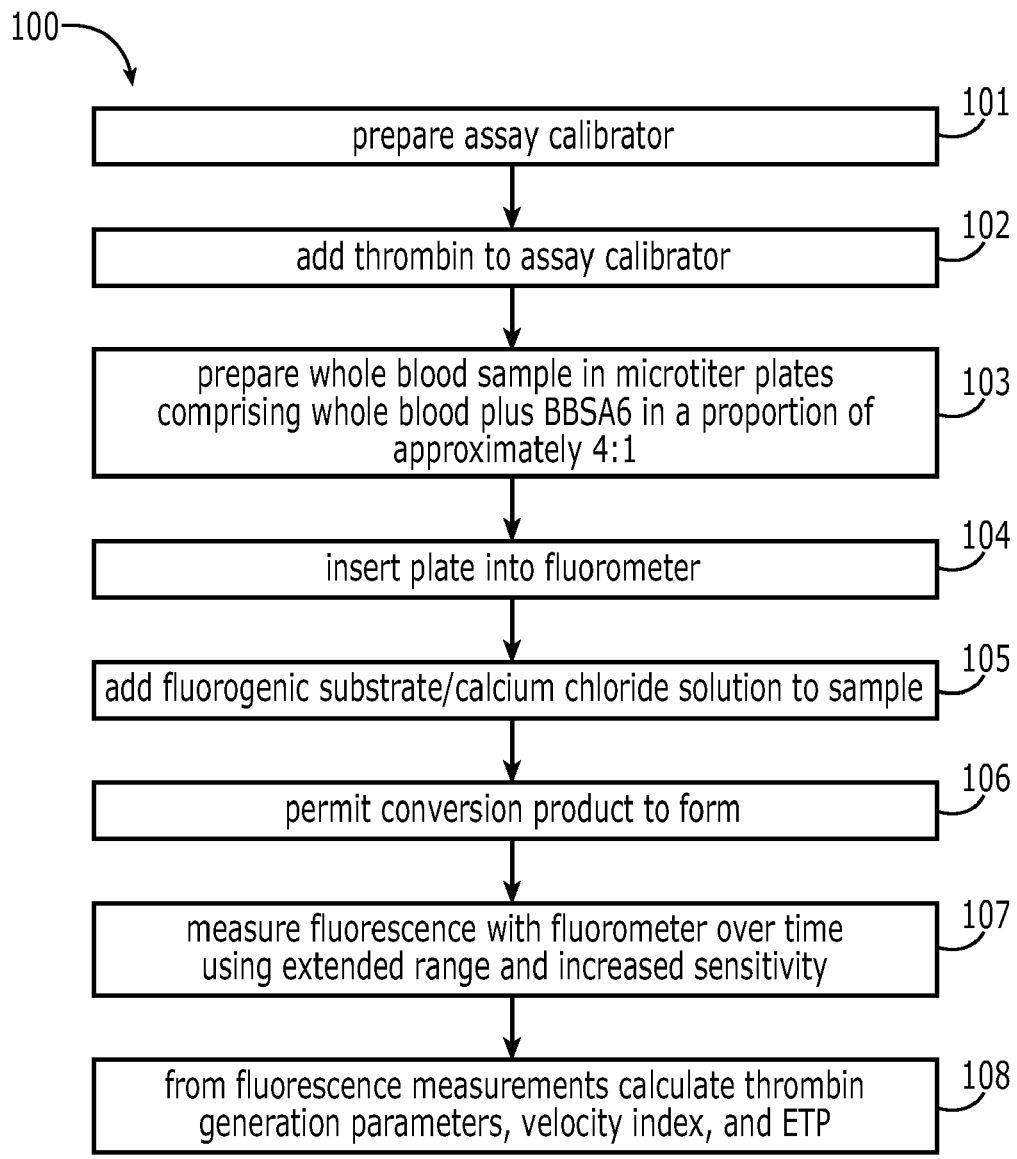
FIG. 1 is a flowchart of an exemplary method of the present invention.
Figure 2:
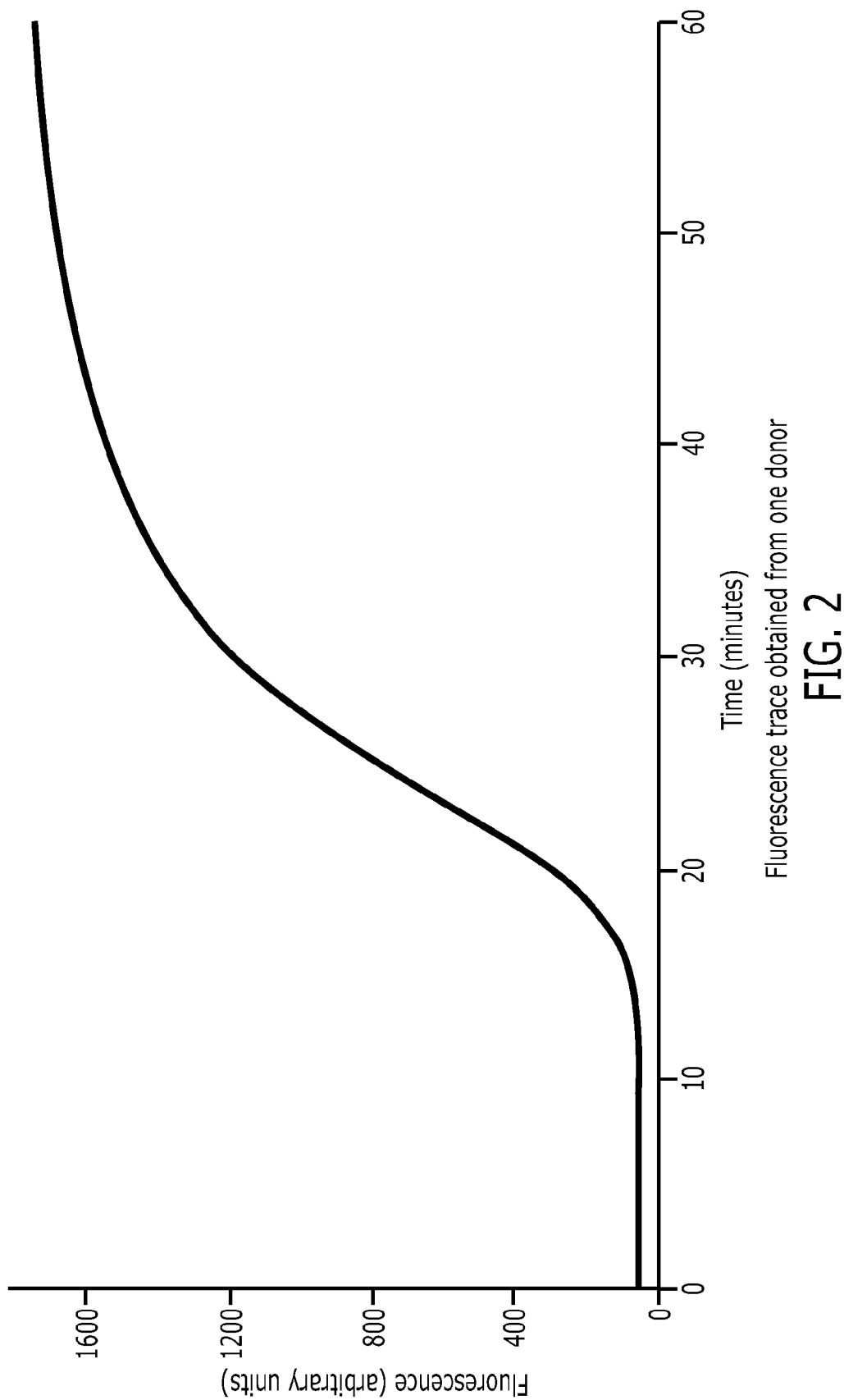
FIG. 2 is a fluorescence trace over time obtained on a sample from a single donor.
Figure 3:
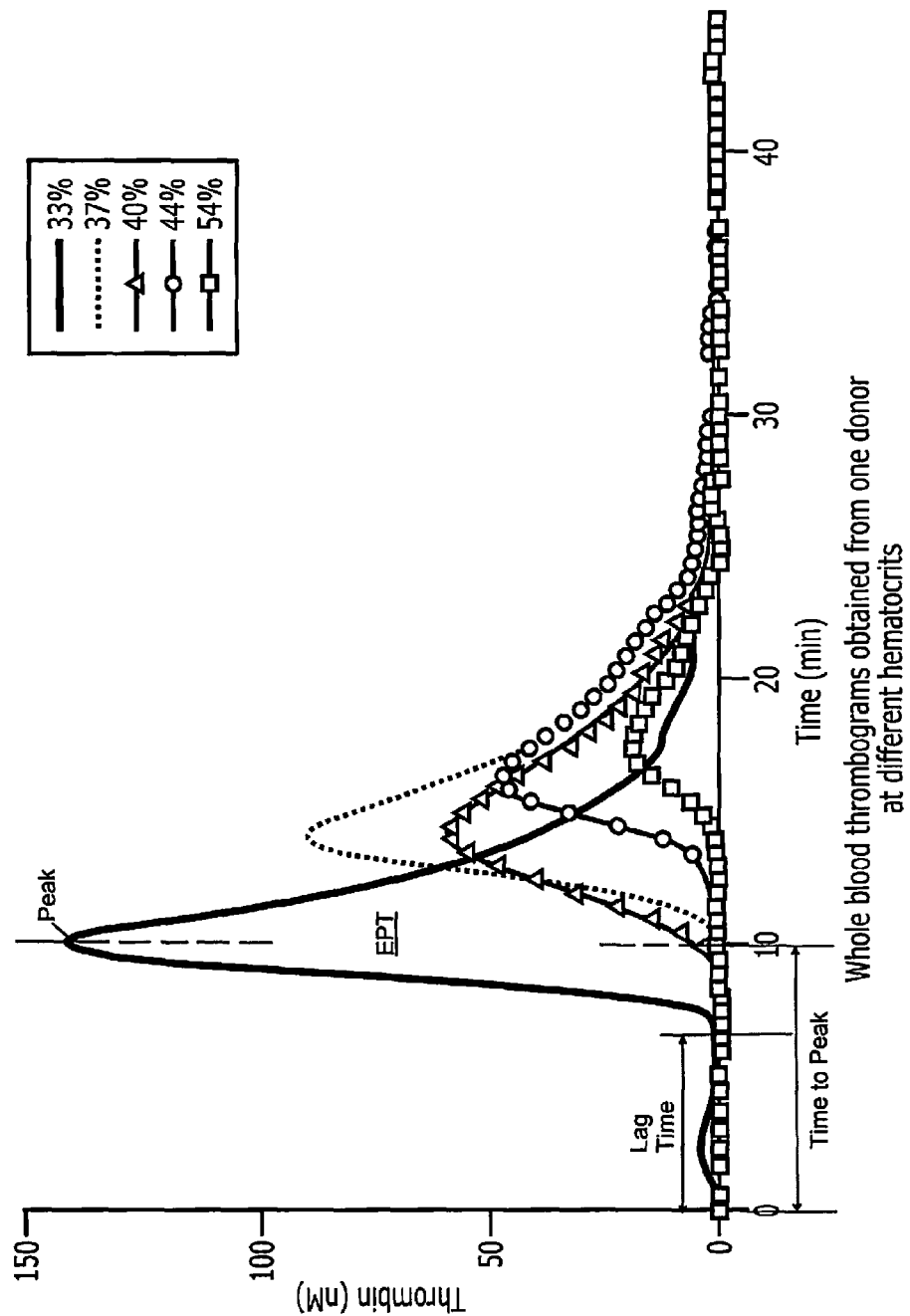
FIG. 3 is a graph of thrombin concentration as a function of time for a single donor at different hematocrits (-, 33%; - -, 37%; ∆, 40%; ○, 44%; and □, 54%).

A description of the preferred embodiments of the present invention will now be presented with reference to FIGS. 1-3.

The method 100 (FIG. 1) of the present invention includes preparing an assay calibrator (block 101) by mixing heat-inactivated platelet-poor plasma and autologous washed red blood cells in PBS without calcium and magnesium to obtain "heat-inactivated whole blood," having substantially the same hematocrit as the original blood sample. Thrombin (20 µl) is then added to the assay calibrator (block 102).

A whole blood sample is prepared that comprises whole blood (WB) plus BBSA6 (HEPES buffer containing 6 g/l BSA) in a proportion of approximately 4:1 (e.g., 80 µl and 20 µl, respectively). The sample is prepared in quintuplicate in 96-well microtiter plates (block 103). Each sample has its own calibrator, comprising 20 µl thrombin and 80 µl WB calibrator in duplicate.

The plate is inserted into a fluorometer (block 104), for example, a Synergy 2 Multi-Mode Microplate Reader fluorometer (BioTek Instruments, Inc., Winooski, Vt.) equipped with a filter set comprising a 360±40 nm excitation and 460±40 nm emission range and a dispenser, although this particular device is not intended as a limitation. The fluorometer will have been altered so as to read emitted fluorescence in extended range mode, increasing the range from a standard range of 0-99,999 relative fluorescence units to an extended range of 0-5,800,000 relative fluorescence units. The sensitivity will also have been substantially increased, for example, from 42 units used when measuring thrombin generation in plasma to 70 units. Further, the parameters of the fluorometer will have been adjusted to read emitted fluorescence from the bottom of the plate.

Thrombin generation is substantially immediately triggered by adding 20 µl of a fluorogenic substrate/calcium chloride solution (block 105). The fluorogenic substrate can comprise, for example, Z-GGR-AMC (Bachem, Switzerland) dissolved to a concentration of 5 mM in a buffer containing 10% DMSO, although this is not intended as a limitation. The buffer can comprise, for example, 20 mM HEPES, 150 mM NaCl, and 60 mg/ml bovine serum albumin (BSA, Sigma).

As known in the art, the reaction includes the cleaving off of a fluorescent group that is then detected by the fluorometer, and a conversion product is formed (block 106). Fluorescence is measured over time, for example, once per 30 sec over 60 min, at 37° C. (block 107), using the adapted fluorometer as described above.

The kinetic data collected are exported to a software package, for example, Microsoft® Excel®, for processing. Among the parameters that can be measured are included thrombin generation parameters such as lag time (min), time to peak (min), peak thrombin concentration (nmol/l), velocity index (nM/min), and endogenous thrombin potential (ETP, nmol/l-min) (block 108), in ways known in the art. Briefly, the fluorescence signal is converted to thrombin concentration by continuous comparison with the signal generated by the thrombin calibrator after compensating for thrombin decay, variability in light absorption, substrate consumption, and inner filter effect, and adjusted for the α2-macroglobulin-thrombin complex activity present in the sample.

This method 100 can also be adapted to other embodiments, such as adding activators (tissue factor, phospholipids), induction of tissue factor expression (e.g., bacterial endotoxin), or inhibitors (e.g., corn trypsin inhibitor, CTI). The current method 100 does not require the addition of exogenous tissue factor (TF) or phospholipids to obtain data for the calculation of TGA parameters; however, if the thrombin generated is very low, TF can be added to the sample to trigger the reaction. Other reagents such as endotoxin or CTI can be included to explore clotting activation by different pathways.

The present method 100 has been used to obtain the following data. FIG. 2 is a fluorescence trace over time obtained on a sample from a single donor. FIG. 3 is a series of thrombin concentration graphs as a function of time for a single donor at different hematocrits. Different hematocrits were obtained after sedimentation of the red blood cells by centrifugation and re-suspension (after wash in PBS) in platelet-poor plasma, using specific volumes to obtain the desired variable hematocrits.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A method for measuring a generation of thrombin in a sample of whole blood as a function of time, the method comprising:
   providing a sample of whole blood;
   adding a fluorogenic substrate and a thrombin activator to the sample of whole blood to form an activated sample;
   forming a conversion product in the activated whole blood sample resulting from the fluorogenic substrate adding step;
   providing a fluorescence detector for reading emitted fluorescence;
   selecting an extended reading range mode of the fluorescence detector for measuring emitted fluorescence resulting in values of measured fluorescence units significantly above those values resulting from a typical operating reading range mode of the fluorescence detector;
   selecting a sensitivity of the fluorescence detector sufficient for delivering stable and consistent measurements within a signal quenching environment of red blood cells;
   measuring fluorescence as a function of time from a fluorescent group released during the formation of the conversion product with the fluorescence detector operating in the extended reading range mode of fluorescence readings and having the selected sensitivity; and
   calculating thrombin generation as a function of time from the fluorescence measuring step, wherein the combination of the extended reading range mode and the increased sensitivity results in fluorescence traces that allow the thrombin generation calculating step to provide a thrombin generation parameter of at least one of a peak value, a time to peak value, and an endogenous potential (ETP).

2. The method recited in claim 1, wherein the fluorescence detector is used with a filter set comprising 360+/−0.40 nm excitation and 460+/−0.40 nm emission range.

3. The method recited in claim 1, wherein the fluorescence is measured at a rate of once per 30 sec for 60 min at 37° C.

4. The method recited in claim 1, wherein the selected sensitivity is about 70 units.

5. The method recited in claim 1, wherein the extended range mode comprises extending the fluorescence readings from a range of 0 to 99,999 to a range of 0 to 5,800,000 units.

6. The method recited in claim 1, further comprising preparing an assay calibrator comprising a mixture of heat-inactivated platelet-poor plasma and autologous washed red blood cells, the mixture having a hematocrit substantially the same as the hematocrit of the whole blood sample.

7. The method recited in claim 1, wherein the whole blood sample comprises whole blood plus HEPES buffer in a proportion of approximately 4:1.

8. The method recited in claim 1, wherein the thrombin activator comprises calcium chloride.

9. The method according to claim 7, wherein the HEPES buffer contains a bovine serum albumin.

10. The method according to claim 1, wherein the fluorescence detector comprises a micro-plate reader styled fluorescence detector, and wherein the fluorescence measuring comprises reading emitted fluorescence from a bottom of a plate of the fluorescence detector.

11. The method according to claim 1, wherein the step of selecting a sensitivity of the fluorescence comprises selecting a sensitivity of a photomultiplier operable with the fluorescence detector.

* * * * *